United States Patent

Arcamone et al.

[11] 4,107,423
[45] Aug. 15, 1978

[54] PROCESS FOR PREPARING DAUNOMYCIN AND ANALOGUES THEREOF

[75] Inventors: Federico Arcamone; Luigi Bernardi; Bianca Patelli; Sergio Penco, all of Milan, Italy

[73] Assignee: Societa Farmaceutici Italia S.p.A., Milan, Italy

[21] Appl. No.: 695,434

[22] Filed: Aug. 14, 1976

[51] Int. Cl.$^2$ ............................................ C07H 15/24
[52] U.S. Cl. ........................................ 536/4; 260/365; 536/17
[58] Field of Search .................... 260/365; 536/4, 17, 536/120

[56] References Cited

U.S. PATENT DOCUMENTS

| | | | |
|---|---|---|---|
| 3,427,300 | 2/1969 | Sarett et al. | 536/4 |
| 3,590,028 | 6/1971 | Arcamone et al. | 536/17 |
| 3,629,231 | 12/1971 | Hough et al. | 536/4 |
| 3,665,018 | 5/1972 | Jolles et al. | 260/365 |
| 3,803,124 | 4/1974 | Arcamone et al. | 536/17 |
| 4,039,663 | 8/1977 | Arcamone et al. | 536/4 |

Primary Examiner—Johnnie R. Brown

Attorney, Agent, or Firm—Hubbell, Cohen, Stiefel & Gross

[57] ABSTRACT

Racemic anthracyclinones of the general formula II

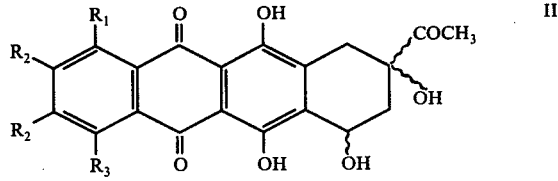

when condensed with 2,3,6-trideoxy-3-trifluoroacetamido-4-0-trifluoroacetyl-α-L-lyxo-pyranosyl chloride in the presence of silver trifluoromethane sulphonate yield an easily separable mixture of equimolar amounts of exclusively the α-glycoside of the 7S : 9S diastereomer and the β-glycoside of the 7R : 9R diastereomer. In this way the biologically important α-glycosides of the 7S : 9S diastereomer of the general formula I (below) are easily prepared from a racemic anthracyclinone.

5 Claims, No Drawings

PROCESS FOR PREPARING DAUNOMYCIN AND ANALOGUES THEREOF

CROSS REFERENCE TO RELATED APPLICATIONS

This application is related to and incorporates by reference the contents of co-pending applications Ser. Nos. 579,901, now U.S. Pat. No. 4,046,878 and 649,825, now U.S. Pat. No. 4,077,988, filed respectively on May 22, 1975 and Jan. 16, 1976, both of which are owned by the assignee of this application.

BACKGROUND OF THE INVENTION

1. Field of the Invention

The invention relates to processes for the preparation of known anthracyline glycosides, including daunomycin, which glycosides are useful as antitumor agents.

2. The Prior Art

Belgian Pat. No. 830,090 which corresponds to U.S. Pat. No. 4,046,878 describes a process for preparing diastereomeric mixtures of the present anthracycline glycosides which are separatable only through a long and tedious procedure. U.S. Pat. No. 4,077,988 (which is not part of the prior art) describes an alternative process which is a total synthesis of optically active anthracyclinones and which eliminates the lengthy separation procedure of the process of said Belgian patent. The present invention, as will be more fully explained below, is an improvement on both said prior processes.

SUMMARY OF THE INVENTION

The present invention provides a new process for the preparation of anthracycline glycosides of the formula I:

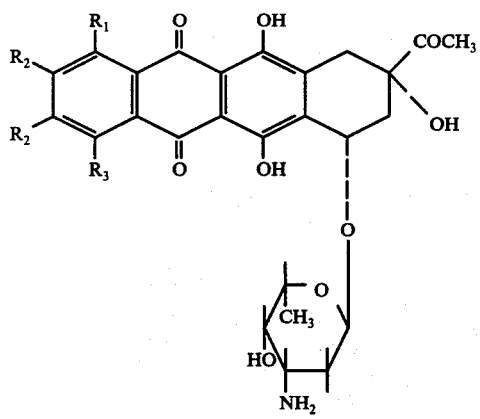

wherein
(a) $R_2$ is hydrogen and $R_1$ and $R_3$ are both methyl, methoxy, chlorine or bromine;
(b) $R_1$ and $R_3$ are both hydrogen and $R_2$ is hydrogen, methyl, methoxy, chlorine or bromine;
(c) $R_1$ and $R_2$ are both hydrogen and $R_3$ is a lower alkoxy group having from 1 to 4 carbon atoms.

Starting from a racemic aglycone of the formula II:

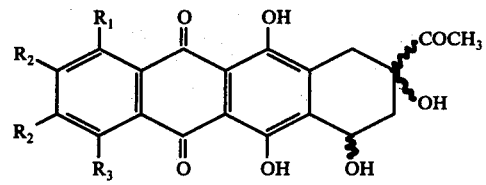

wherein $R_1$, $R_2$ and $R_3$ are as defined above, and provided that the 7,9-diol has the cis configuration, Belgian Pat. No. 830,090 and U.S. Pat. No. 4,046,878, describe a process for the preparation of anthracycline glycosides of the formulae I and III, together with their respective β-anomers:

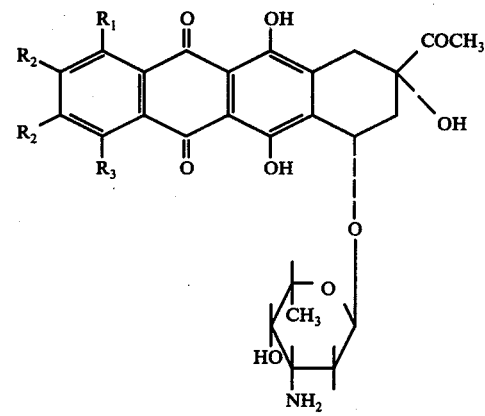

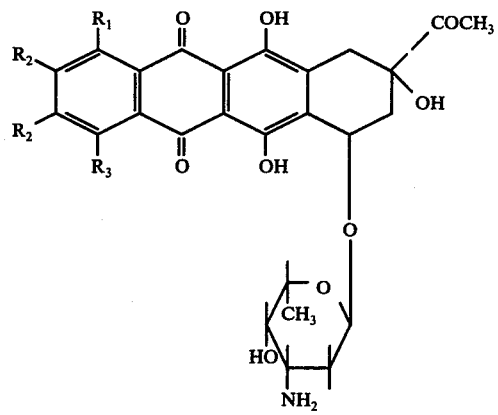

which process comprises condensing the racemic aglycone of formula II with 2,3,6-trideoxy-3-trifluoroacetamido-4-O-trifluoroacetyl-α-L-lyxo-pyranosyl chloride in an anhydrous solvent in the presence of mercuric oxide and/or mercuric bromide and a molecular sieve. According to that process, after having been separated by chromatography from their respective β-anomers, the compound I (that is α(−) daunosaminyl (+) anthracyclinone, in which the (+) anthracyclinone has the 7S : 9S configuration) and the compound III (that is α(−) daunosaminyl (−) anthracyclinone, in which the (−) anthracyclinone has the 7R : 9R configuration, also referred to by applicants as the 7,9-bis-epi-anthracyclinone), are obtained as a mixture. The separation of these very similar diastereomeric substances is, however, a lengthy and tedious operation. In order to avoid this tedious separation, an alternative process was developed and is described in detail in U.S. Pat. No. 4,077,988.

The alternative process described in U.S. Pat. No. 4,077,988 is a total synthesis of optically active anthracyclinones of (7S : 9S) and (7R : 9R) configuration, which are subsequently condensed with 2,3,6-trideoxy-3-trifluoroacetamido-4-O-trifluoroacetyl-α-L-lyxo-pyranosyl chloride to give, directly, compounds of the general formula I or III in pure form.

It has now been surprisingly found, in accordance with the present invention, that the condensation of 2,3,6-trideoxy-3-trifluoroacetamido-4-O-trifluoroacetyl-α-L-lyxo-pyranosyl chloride with a racemic aglycone of the formula II, in an aprotic solvent such as dichloromethane, chloroform, benzene, acetonitrile or dioxane and in the presence of an equimolar amount of silver trifluoromethane sulfonate ($AgSO_3CF_3$), in respect to the sugar compound yields, in a few minutes, a 50:50 mixture of the protected 7S : 9S)-α-glycosides IVa and (7R : 9R)-β-glycosides Va:

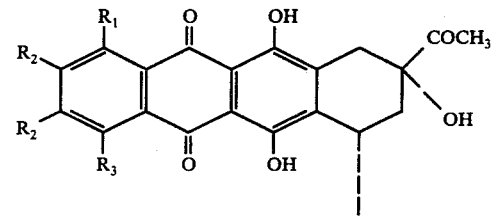

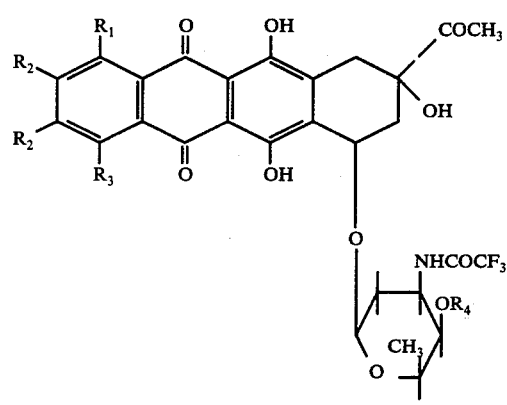

IVa ; $R_4$ = $COCF_3$       Va ; $R_4$ = $COCF_3$
IVb ; $R_4$ = H              Vb ; $R_4$ = H

In other words, the 7S : 9S moiety of the racemic aglycone unexpectedly reacts with the reactive protected sugar in a stereospecific manner to produce the α-glycosides IVa exclusively, whereas the 7R : 9R moiety of the racemic aglycone produces the β-glycosides Va exclusively.

These glycosides are however much more conveniently isolated as the N-monotrifluoroacetates, IVb and Vb.

It is apparent to those skilled in the art that, whereas in the process described in Belgian Pat. No. 830,090 and U.S. Pat. No. 4,046,878 one ends up with a mixture of α-glycosides of enantiomeric alcohols of the formulae I and III having very similar properties and therefore only difficultly separatable, in the present process one ends up with a mixture of the α-glycoside of one single enantiomer and the β-glycoside of the other enantiomer. Since the physical properties of the α and β-glycosides are vastly different, it is quite easy to separate the two glycosides IVb and Vb either by crystallization or by chromatography.

In this way it is therefore possible to obtain in good yields the α-(—) daunosaminyl derivatives IVb of the (7S : 9S) anthracyclinones by employing racemic anthracyclinones as starting materials. The subsequent mild alkaline hydrolysis of the IVb derivatives with 0.1N NaOH at room temperature for 30 minutes affords the desired compounds of formula I.

The present process can thus be used to resolve the racemic aglycones of formula II into its enantiomers by a very mild acid hydrolysis of the glycosidic bond in the compounds of formulae IVb and Vb.

DESCRIPTION OF THE PREFERRED EMBODIMENTS

The following examples, wherein all parts given are by weight, unless otherwise indicated, are presented to merely illustrate the process of the invention, without, however being a limitation thereof.

EXAMPLE 1

α-N-trifluoroacetyl-4-demethoxy-daunomycin (IVb, $R_1$=$R_2$=$R_3$=H) and β-N-trifluoroacetyl-4-demethoxy-7,9-bis-epi-daunomycin (Vb; $R_1$=$R_2$=$R_3$=H).

To a suspension of 1 g. of racemic 4-demethoxy-daunomycinone (II; $R_1$=$R_2$=$R_3$=H) and 1.2 g. of 2,3,6-trideoxy-3-trifluoroacetamido-4-O-trifluoroacetyl-α-L-lyxo-pyranosyl chloride in 150 ml. of dichloromethane there was added, over a period of 10 minutes, in the dark, under stirring and at room temperature, 1 g. of silver trifluoromethane sulfonate dissolved in 20 ml. of diethyl ether. After 20 minutes, an excess of a saturated sodium bicarbonate solution was added, with stirring. The organic layer was separated off and concentrated under vacuum. The residue which was obtained was taken up in methanol and heated at 50° C. for 30 minutes. Evaporation of the methanol solvent left a residue that was taken up in chloroform and washed with saturated sodium bicarbonate solution. Evaporation of the chloroform solvent left a residue that was chromatographed on a short silica column, eluting first with chloroform and then with a mixture of 95 parts of chloroform and 5 parts of acetone (v : v).

The first eluate yielded, on crystallization from chloroform, 0.7 g. of α-N-trifluoroacetyl-4-demethoxy-demethoxy-daunomycin; m.p. 155°–158° C.; $[\alpha]_D^{20}$ = +196° (c = 0.1 dioxane).

β-N-trifluoroacetyl-4-demethoxy-7,9-bis-epi-daunomycin, which was eluted next was crystallized from a mixture of tetrahydrofuran and diethyl ether 1:5 (v/v) to yield 0.65 g; m.p. 165°–167° C; $[\alpha]_D^{20}$ = —270° (c = 0.1 dioxane).

EXAMPLE 2

4-Demethoxy-daunomycin (I; $R_1$=$R_2$=$R_3$=H)

0.6 g. of α-N-trifluoroacetyl-4-demethoxy-daunomycin (IVb; $R_1$=$R_2$=$R_3$=H) prepared as described in Example 1 was dissolved in 40 ml. of 0.1N NaOH and kept at room temperature for 30 minutes. The solution was brought to pH 8 with HCl and extracted with chloroform. Evaporation of the solvent left a residue that was taken up in 5 ml of a mixture of chloroform-methanol 3:2 (v/v). Methanolic 0.1N HCl was added to adjust the pH to 4.5, after which sufficient diethyl ether was added to precipitate 0.35 g of the hydrochloride of 4-demethoxy-daunomycin; m.p. 183°-185° C; $[\alpha]_D^{20} = +210°$ ($c = 0.1$ CH$_3$OH).

EXAMPLE 3

α-N-trifluoroacetyl-4-demethoxy-2,3-dimethyl-daunomycin (IVb; R$_1$=R$_3$=H; R$_2$=CH$_3$) and
β-N-trifluoroacetyl-4-demethoxy-2,3-dimethyl-7,9-bis-epi-daunomycin (Vb; R$_1$=R$_3$=H; R$_2$=CH$_3$).

Operating in accordance with the procedure of Example 1, but employing racemic 4-demethoxy-2,3-dimethyldaunomycinone (II; R$_1$=R$_3$=H; R$_2$=CH$_3$) there were obtained α-N-trifluoroacetyl-4-demethoxy-2,3-dimethyl-daunomycin; m.p. 233°-235° C.; $[\alpha]_D^{20} = +181°$ (c =0.1 dioxane) and β-N-trifluoroacetyl-4-demethoxy-2,3-dimethyl-7,9-bis-epi-daunomycin.

EXAMPLE 4

4-Demethoxy-2,3-dimethyl-daunomycin (I; R$_1$=R$_3$=H; R$_2$=CH$_3$).

Operating in accordance with the procedure of Example 2 but employing a α-N-trifluoroacetyl-4-demethoxy-2,3-dimethyl-daunomycin (prepared as described in Example 3) there was obtained 4-demethoxy-2,3-dimethyl-daunomycin hydrochloride; m.p. 190°-192° C.; $[\alpha]_D^{20} = +180°$ (c = 0.1 CH$_3$OH).

EXAMPLE 5

α-N-trifluoroacetyl-4-demethoxy-2,3-dichloro-daunomycin (IVb; R$_1$=R$_3$=H; R$_2$=Cl) and
β-N-trifluoroacetyl-4-demethoxy-2,3-dichloro-7,9-bis-epi-daunomycin (Vb; R$_1$=R$_3$=H; R$_2$=Cl).

Operating in accordance with the procedure of Example 1, but employing racemic 4-demethoxy-2,3-dichloro-daunomycinone (II; R$_1$=R$_3$=H; R$_2$=Cl) there were obtained α-N-trifluoroacetyl-4-demethoxy-2,3-dichloro-daunomycin; m.p. 238°-240° Cl; $[\alpha]_D^{20} = +175°$ (c = 0.1 CHCl$_3$) and β-N-trifluoroacetyl-4-demethoxy-2,3-dichloro-7,9-bis-epi-daunomycin.

EXAMPLE 6

4-Demethoxy-2,3-dichloro-daunomycin (I; R$_1$=R$_3$=H; R$_2$=Cl).

Operating in accordance with the procedure of Example 2 but employing α-N-trifluoroacetyl-4-demethoxy-2,3-dichloro-daunomycin (prepared as in Example 5) there was obtained 4-demethoxy-2,3-dichloro-daunomycin hydrochloride; $[\alpha]_D^{20} = +180°$ (c = 0.1 CH$_3$OH).

EXAMPLE 7

α-N-trifluoroacetyl-daunomycin (IVb; R$_1$=R$_2$=H; R$_3$=OCH$_3$) and
β-N-trifluoroacetyl-7,9-bis-epi-daunomycin (Vb; R$_1$=R$_2$=H; R$_3$=OCH$_3$).

Operating in accordance with the procedure of Example 1, but employing racemic daunomycinone [Can.J.Chem. 51, 466 (1973)] (II; R$_1$=R$_2$=H; R$_3$=OCH$_3$), there were obtained α-N-trifluoroacetyl-daunomycin, m.p. 169°-171° C.; $[\alpha]_D^{20} = +220°$ (c = 0.1 dioxane) and β-N-trifluoroacetyl-7,9-bis-epi-daunomycin.

EXAMPLE 8

Daunomycin (I; R$_1$=R$_2$=R; R$_3$=OCH$_3$).

Operating in accordance with the procedure of Example 2, but employing α-N-trifluoroacetyl-daunomycin (prepared as in Example 7), daunomycin hydrochloride m.p. 188°-189° C.; $[\alpha]_D^{20} = +240°$ (c = 0.1 CH$_3$OH) was obtained.

EXAMPLE 9

4-Demethoxy-daunomycinone (II; R$_1$=R$_2$=R$_3$=H)

1.5 g. of α-N-trifluoroacetyl-4-demethoxy-daunomycin (IVb; R$_1$=R$_2$=R$_3$=H) which was prepared as described in Example 1 were dissolved in 50 ml. of acetone containing 50 ml. of 0.25N HCl. The solution was kept at 50° C. for 30 minutes, after which the acetone was evaporated in vacuo and the solution filtered to yield (90%) 4-demethoxy-daunomycinone, m.p. 185°-187° C.; $[\alpha]_D^{20} = +168°$ (c = 0.1 dioxane).

EXAMPLE 10

4-Demethoxy-7,9-bis-epi-daunomycinone

Operating in accordance with the procedure of Example 9, but employing β-N-trifluoroacetyl-4-demethoxy-7,9-bis-epi-daunomycin (Vb; R$_1$=R$_2$=R$_3$=H), which was prepared as described in Example 1, 4-demethoxy-7,9-bis-epi-daunomycinone was obtained; m.p. 185°-187° C.; $[\alpha]_D^{20} = -167°$ (c = 0.1 dioxane).

By following the procedure described in Example 1, and choosing the appropriate racemic aglycones as starting materials, the following daunomycin analogues were obtained:

α-N-trifluoroacetyl-2,3-dibromo-4-demethoxydaunomycin,
β-N-trifluoroacetyl-2,3-dibromo-4-demethoxy-7,9-bis-epi-daunomycin,
α-N-trifluoroacetyl-2,3-dimethoxy-4-demethoxydaunomycin,
β-N-trifluoroacetyl-2,3-dimethoxy-4-demethoxy-7,9-bis-epi-daunomycin,
α-N-trifluoroacetyl-1-methoxydaunomycin,
β-N-trifluoroacetyl-1-methoxy-7,9-bis-epidaunomycin,
α-N-trifluoroacetyl-1,4-dichloro-4-demethoxydaunomycin,
β-N-trifluoroacetyl-1,4-dichloro-4-demethoxy-7,9-bis-epi-daunomycin,
α-N-trifluoroacetyl-1,4-dibromo-4-demethoxydaunomycin,
β-N-trifluoroacetyl-1,4-dibromo-4-demethoxy-7,9-bis-epi-daunomycin,
α-N-trifluoroacetyl-1,4-dimethyl-4-demethoxydaunomycin, and
β-N-trifluoroacetyl-1,4-dimethyl-4-demethoxy-7,9-bis-epi-daunomycin.

Variations and modifications can, of course, be made without departing from the spirit and scope of the invention.

Having thus described our invention what we desire to secure by Letters Patent and hereby claim is:

1. A process for preparing a compound of formula I

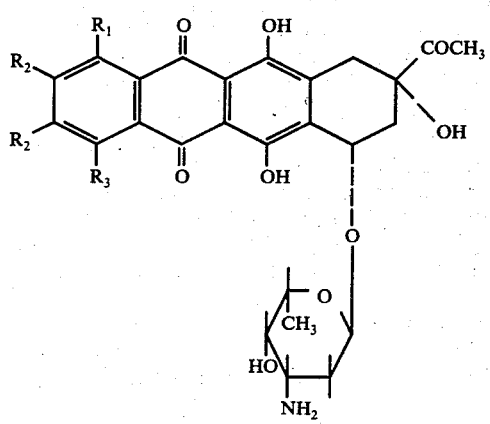

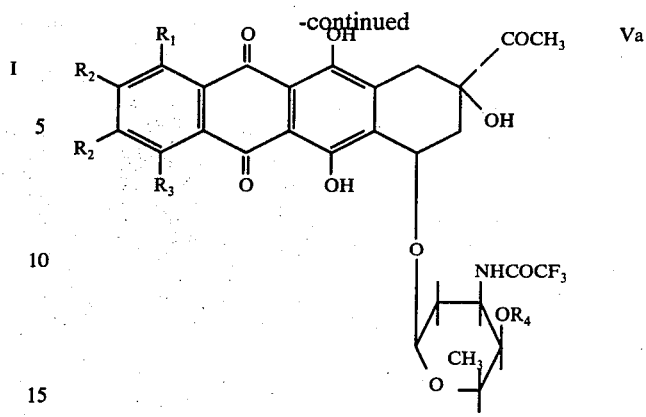

wherein
(a) $R_2$ is hydrogen and $R_1$ and $R_3$ are both methyl, methoxy, chlorine or bromine;
(b) $R_1$ and $R_3$ are both hydrogen and $R_2$ is hydrogen, methyl, methoxy, chlorine or bromine; and
(c) $R_1$ and $R_2$ are both hydrogen and $R_3$ is a lower alkoxy group having from 1 to 4 carbon atoms, said process comprising condensing a racemic aglycone of formula II:

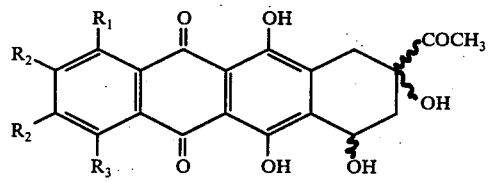

wherein $R_1$, $R_2$ and $R_3$ are as defined above, with 2,3,6-trideoxy-3-trifluoroacetamido-4-O-trifluoroacetyl-α-L-lyxo-pyranosyl chloride, in an aprotic solvent and in presence of an equimolecular amount of silver trifluoromethane sulfonate in respect to the sugar compound, to give a mixture of the protected (7S : 9S)-α-glycosides (IVa) and (7R : 9R)-β-glycosides (Va):

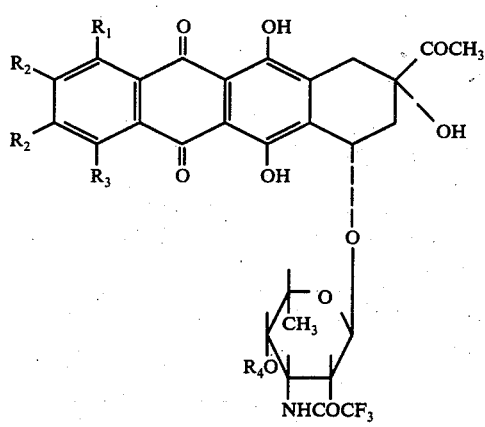

wherein $R_1$, $R_2$ and $R_3$ are as defined above and $R_4$ is a —COCF$_3$ group, treating said mixture with methanol to remove the —COCF$_3$ group from the sugar moiety and thereby obtain a further mixture of the respective N-trifluoroacetyl derivatives of formulae IVb and Vb:

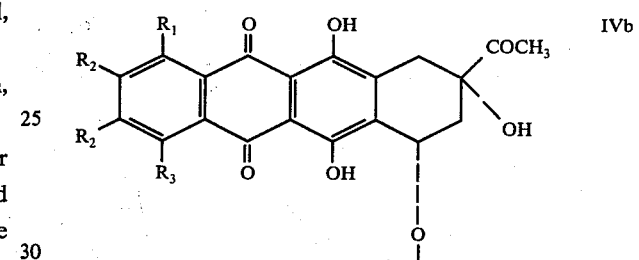

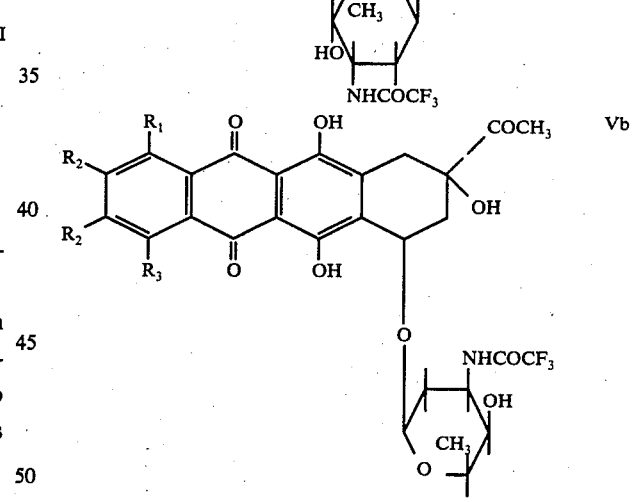

subjecting said further mixture to chromatography on a silica gel column using as the eluent therefor first chloroform and then a mixture of chloroform-acetone 95:5 (v/v), to obtain the (7S : 9S)-α-glycosides of formula IVb and then subjecting same to a mild alkaline hydrolysis at room temperature for about 30 minutes to thereby obtain a compound of formula I as the hydrochloride.

2. A process according to claim 1, wherein the mild alkaline hydrolysis is effected with 0.1N NaOH.

3. A process according to claim 1, for obtaining the (7R : 9R)-β-glycosides of the formula Vb.

4. A process for resolving the racemic aglycones of formula II, wherein the (7S : 9S)-α-glycosides of formula IVb and the (7R : 9R)-β-glycosides of formula Vb, which are obtained and separated according to the procedure of claim 1, are separately treated in acetone with a mild acidic hydrolyzing agent to cleave the glycosidic bond and thereby obtain the enantiomeric (7S : 9S) and (7R : 9R) aglycones of formula II.

5. A process according to claim 4, wherein the mild acidic hydrolyzing agent is 0.25N HCl.

* * * * *

UNITED STATES PATENT OFFICE
CERTIFICATE OF CORRECTION

Patent No. 4,107,423              Dated August 15, 1978

Inventor(s) Federico Arcamone et al

It is certified that error appears in the above-identified patent and that said Letters Patent are hereby corrected as shown below:

Column 1, lines 11-12: "4,077,988, filed respectively on May 22, 1975 and Jan. 16, 1976, both" should read -- 4,077,988, both --.

Column 4, lines 51-52: "$\alpha$-N-trifluoroacetyl-4-demethoxy-demethoxy-daunomycin" should read -- $\alpha$-N-trifluoroacetyl-4-demethoxy-daunomycin --.

Column 5, line 25: "employing a" should read -- employing --;
line 41: "238°-240° Cl;" should read -- 238°-240° C; --.

Column 6, line 4: "$R_1=R_2=R$" should read -- $R_1=R_2=H$; --.

Signed and Sealed this

Twelfth Day of June 1979

[SEAL]

Attest:

RUTH C. MASON
*Attesting Officer*

DONALD W. BANNER
*Commissioner of Patents and Trademarks*